United States Patent
Abe et al.

(10) Patent No.: US 7,113,841 B2
(45) Date of Patent: Sep. 26, 2006

(54) IMPLANT FORMING METHOD

(75) Inventors: Keita Abe, Tokyo (JP); Shingo Shiotani, Tokyo (JP); Motomasa Kato, Tokyo (JP); Takamitsu Yoshida, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 288 days.

(21) Appl. No.: 10/227,224

(22) Filed: Aug. 26, 2002

(65) Prior Publication Data

US 2003/0042641 A1 Mar. 6, 2003

(30) Foreign Application Priority Data

Aug. 30, 2001 (JP) ............................. 2001-262196
Nov. 22, 2001 (JP) ............................. 2001-357535

(51) Int. Cl.
*A61F 2/02* (2006.01)
*G06F 19/00* (2006.01)

(52) U.S. Cl. .................... 700/118; 700/97; 700/98; 700/117; 700/119; 623/16.11; 623/17.19; 623/23.51; 623/901

(58) Field of Classification Search ................. 700/95, 700/97, 182, 98, 117, 118, 119, 120; 623/23.51, 623/23.56, 16.11, 17.18, 17.19, 901, 912, 623/914; 264/40.1, 112, 113, 497; 606/60; 600/407
See application file for complete search history.

(56) References Cited

U.S. PATENT DOCUMENTS

| 4,873,707 | A | * | 10/1989 | Robertson ..................... 378/18 |
| 4,976,737 | A | * | 12/1990 | Leake ........................ 623/901 |
| 5,150,304 | A | * | 9/1992 | Berchem et al. ............ 623/901 |
| 5,156,777 | A |   | 10/1992 | Kaye et al. |
| 5,231,470 | A |   | 7/1993 | Koch |
| 5,370,692 | A |   | 12/1994 | Fink et al. |
| 5,518,680 | A |   | 5/1996 | Cima et al. |
| 5,639,402 | A | * | 6/1997 | Barlow et al. ............... 264/497 |
| 5,687,788 | A |   | 11/1997 | Caldarise et al. |
| 5,768,134 | A | * | 6/1998 | Swaelens et al. ........... 623/901 |
| 5,824,085 | A | * | 10/1998 | Sahay et al. ................. 623/914 |
| 5,869,170 | A |   | 2/1999 | Cima et al. |
| 6,036,777 | A |   | 3/2000 | Sachs |
| 6,083,264 | A | * | 7/2000 | Wood et al. .............. 623/16.11 |
| 6,112,109 | A | * | 8/2000 | D'Urso ........................ 623/901 |
| 6,176,874 | B1 |   | 1/2001 | Vacanti et al. |
| 6,177,034 | B1 |   | 1/2001 | Ferrone |
| 6,183,515 | B1 | * | 2/2001 | Barlow et al. ........... 623/16.11 |
| 6,254,639 | B1 |   | 7/2001 | Peckitt |

FOREIGN PATENT DOCUMENTS

DE 19945529 4/2001

(Continued)

OTHER PUBLICATIONS

English Language Abstract of EP 0 255 797.

(Continued)

*Primary Examiner*—Albert W. Paladini
*Assistant Examiner*—Charles Kasenge
(74) *Attorney, Agent, or Firm*—Greenblum & Bernstein, P.L.C.

(57) ABSTRACT

An implant designing method to be applied to a body of bone which has a bone deficient portion, wherein the bone being substantially symmetric with respect to a plane of symmetry, includes generating three-dimensional data of the bone based on a plurality of pieces of tomographic data of the bone, and estimating a shape of a bone that is to exist at the bone deficient portion using part of the three-dimensional data corresponding to a symmetrical part of the bone deficient portion.

15 Claims, 8 Drawing Sheets

FOREIGN PATENT DOCUMENTS

| | | |
|---|---|---|
| DE | 10006851 | 8/2001 |
| EP | 0097001 | 12/1983 |
| EP | 0255797 | 2/1988 |
| EP | 0672395 | 9/1995 |
| EP | 1059153 | 12/2000 |
| JP | 5-192362 | 8/1993 |
| JP | 7-277790 | 10/1995 |
| WO | 89/11257 | 11/1989 |
| WO | 95/07509 | 3/1995 |
| WO | 98/12995 | 4/1998 |
| WO | 01/85040 | 11/2001 |

OTHER PUBLICATIONS

"A Comparison of the Shapes of Hydroxyapatite Implants Before and After Implantation", Abe et al., published online on Apr. 3, 2002 in Wiley InterScience <www.interscience.wiley.com>, pp. 312-318.

* cited by examiner

IMPLANT FORMING METHOD

BACKGROUND OF THE INVENTION

The present invention relates to a method for forming a three-dimensional implant.

Conventionally, when a body of bone, for example bones of skull, cheek bone, jaw bone or the like is partially lost, implants made of artificial material are implanted in the deficient part, and fixed thereat (reconstruction of deficient portion of bone).

In the conventional art of reconstruction of the deficient bone, material and shape of the implant is very important.

Regarding the material, ceramics which have excellent biocompatibility are widely used.

Regarding the shape, the implant is conventionally formed as follows.

Firstly, based on CT (Computed Tomography) data of a body of bone having a deficient portion, a model corresponding to the body of bone is formed using wood or the like. Then, in a deficient portion of the model, paper-mache pulp or the like is filled to obtain a shape of an implant (i.e., the shape of body of bone to be located at the deficient portion).

When the shape of the implant is determined in such a manner, however, sufficient reproductivity cannot be obtained. For example, bones of skull are typically reproduced as a continuum of smooth spheres. However, the bones of skull are not usually the continuum of the smooth spheres, and curvatures are different at various points. Therefore, the implant which is formed as the continuum of the smooth spheres has less reproductivity. Regarding the cheek bone or jaw bone, it is more difficult to achieve the high reproductivity.

In another case, the shape of an implant is determined as follows.

Firstly, CT images are obtained with respect to a plurality of cross sections of a body of bone having a deficient portion. Then, plate members (i.e., a plurality of slices) made of wood are formed to have shapes corresponding to the body of bone of the cross sections, respectively.

By stacking the plate members, and making the same adhered together, a model corresponding to the entire body of bone having the deficient portion is formed.

Then, at the deficient portion of the model, paper-mache pulp or the like is filled to obtain a shape of the bone which should exist at the deficient portion. The model formed as above has stepped portions, at its side ends, corresponding to the thickness of the plate members.

Next, using resin material, the model is molded to form a female mold. Then, using the female mold, a male mold made of resin is formed. Then, the steps at the side ends of the male mold are cut out using a cutter or the like so that the male mold has a smooth shape without stepped portions. The thus obtained smooth shape is regarded as the shape of the implant.

When the shape of the implant is determined in such a manner, the following deficiencies are known to arise.

In the above-described method, the model is formed using plate members. Since each plate member is relatively thick, it is difficult to form the model of the body of bone having the deficient portion accurately.

Further, according to the above method, the side end of the male mold is grinded down using a cutter to obtain a smooth surface. However, the actual shape of the body of bone at a surface where the bone is cut is not taken into consideration. Such an implant has less shape compatibility with respect to the body of bone.

If a thinner plate is used, it is possible to improve the shape compatibility of the model. However, there is a limitation in reducing the thickness of each plate member, and it would be difficult to obtain sufficient shape compatibility. Further, if the thinner plate members are used to form the model, it will take a relatively long time for forming a model. Therefore, such a method cannot apply to a condition where the deficient condition cannot remain for a considerable period.

SUMMARY OF THE INVENTION

The present invention is advantageous in that it provides an improved method for forming an implant having an excellent reproductivity of a missing portion of a bone.

The present invention is also advantageous in that, it provides a method for forming an implant which has an excellent shape suitability to a body of bone having a deficient portion.

According to an embodiment of the present invention, there is provided an implant designing method to be applied to a body of bone which has a bone deficient portion, the bone being substantially symmetric with respect to a plane of symmetry. The method includes generating three-dimensional data of the bone based on a plurality of pieces of tomographic data of the bone, and estimating a shape of a bone that is to exist at the bone deficient portion using part of the three-dimensional data corresponding to a symmetrical part of the bone deficient portion.

Since the missing portion to fit the deficient portion is estimated based on the symmetrical part, an implant having excellent shape suitability can be obtained.

In a particular case, the body of bone is a skull. Of course, the body of bone is not limited to the skull, but any bone can be subject to the method as far as it is symmetric with respect to a certain plane.

According to an embodiment, a slicing interval of the tomographic data used for generating the three-dimensional data is within a range of 0.1 mm through 5 mm.

According to another aspect, there is provided an implant forming method for forming an implant based on a design according to the above-described method, and further includes (a) forming a layer composed of an ingredient powder, and (b) hardening a reactant liquid by chemically reacting the ingredient powder with a reactant liquid in accordance with the shape of the implant in accordance with the design. The forming and the making are repeated to stack a plurality of the layers to form an implant formed of the hardened portion of the layers of the ingredient powder.

Optionally, the porosity of the implant is within a range of 10 vol % through 90 vol %.

According to a further aspect of the invention, there is provided an implant designing method to be applied to a bone body which has a bone deficient portion, the bone being in substantial symmetry with respect to a plane of symmetry, which includes generating three-dimensional data of the bone body based on a plurality of pieces of tomographic data of the bone, and estimating a shape of the implant to be implanted at the bone deficient portion based on the three-dimensional data using a symmetric property of the bone body.

According to another aspect of the invention, there is provided an implant designing method to be applied to a bone body having a bone deficient portion, which includes generating three-dimensional data of the bone body, estimating the shape of an implant to be implanted to the bone deficient portion, and modifying the three-dimensional data such that at least a part of the implant in a circumferential direction has a shape that fits a corresponding portion of a bone cutting surface of the bone body.

According to this method, only with a slight processing of the obtained implant, it fits the deficient portion.

Optionally, the estimating includes designing a shape of the implant that matches the shape of the outline of the bone cutting surface on the outer surface of the bone body, the implant having a substantially fixed shape in a direction of thickness thereof, and the modifying includes overlapping the data representing at least the bone cutting surface of the bone body and the data of the implant, and eliminating data of the implant corresponding to a portion overlapping the bone body.

Still optionally, the step of estimating may include generating outline data representing the outer surface of the implant so as to match with the shape of the outline of the bone cutting surface on the outer surface of the bone body, estimating the shape of the implant that has a predetermined thickness and a substantially fixed shape in the direction of thickness, using the outline data, and eliminating, from the estimated shape data, data representing a portion overlapping the bone body so that the implant fits the shape of the bone cutting surface.

Alternatively, the step of estimating may include generating outline data representing the outer surface of the implant so as to match with the shape of the outline of the bone cutting surface on the outer surface of the bone body, estimating the shape of the implant that has a predetermined thickness and a substantially fixed shape in the direction of thickness, using the outline data, comparing data representing the shape of the implant which is generated in the estimating with at least part of the three-dimensional data representing the bone cutting surface, and compensating for the data representing the shape of the implant in accordance with a comparison result of the comparing so that the implant fits the shape of the bone cutting surface.

Alternatively, the step of estimating may include generating outline data representing the outer surface of the implant so as to match with the shape of the outline of the bone cutting surface on the outer surface of the bone body, estimating the shape of the implant that has a predetermined thickness and a substantially fixed shape in the direction of thickness, using the outline data, and eliminating, from the estimated shape data, data representing a portion overlapping the bone body so that the implant fits the shape of the bone cutting surface.

Still alternatively, the step of estimating may further include generating outline data representing the outer surface of the implant so as to match with the shape of the outline of the bone cutting surface on the outer surface of the bone body, estimating the shape of the implant that has a predetermined thickness and a substantially fixed shape in the direction of thickness, using the outline data, comparing data representing the shape of the implant which is generated in the estimating with at least part of the three-dimensional data representing the bone cutting surface, and compensating for the data representing the shape of the implant in accordance with a comparison result of the comparing so that the implant fits the shape of the bone cutting surface.

In the above method, if the implant is applied to the bone deficient portion, the outer surface of the bone body and the outer surface of the implant come to substantially the same surface position.

Further optionally, the bone body is substantially symmetrical with respect to a predetermined plane, a shape of an implant to be implanted at the bone deficient portion being estimated using shape data representative of a portion symmetrical to the bone deficient portion of the three-dimensional data with respect to a substantial symmetry plane of the three-dimensional data.

In a particular case, the body of bone includes a skull.

Optionally, a slicing interval of the topographic data to be used for generating the three-dimensional data is 0.1 mm through 5 mm.

According to another aspect of the invention, there is provided an implant forming method for forming an implant based on a design according to the above method, and further includes (a) forming a layer composed of an ingredient powder, and (b) hardening a reactant liquid by chemically reacting the ingredient powder with a reactant liquid in accordance with the shape of the implant in accordance with the design. The forming and the making are repeated to stack a plurality of the layers to form an implant formed of the hardened portion of the layers of the ingredient powder.

Preferably, the porosity of the implant is within a range of 10 vol % through 90 vol %.

DETAILED DESCRIPTION OF THE EMBODIMENTS

Hereinafter, a method of forming a three-dimensional implant according to an embodiment will be described with reference to the accompanying drawings.

Figure 1:
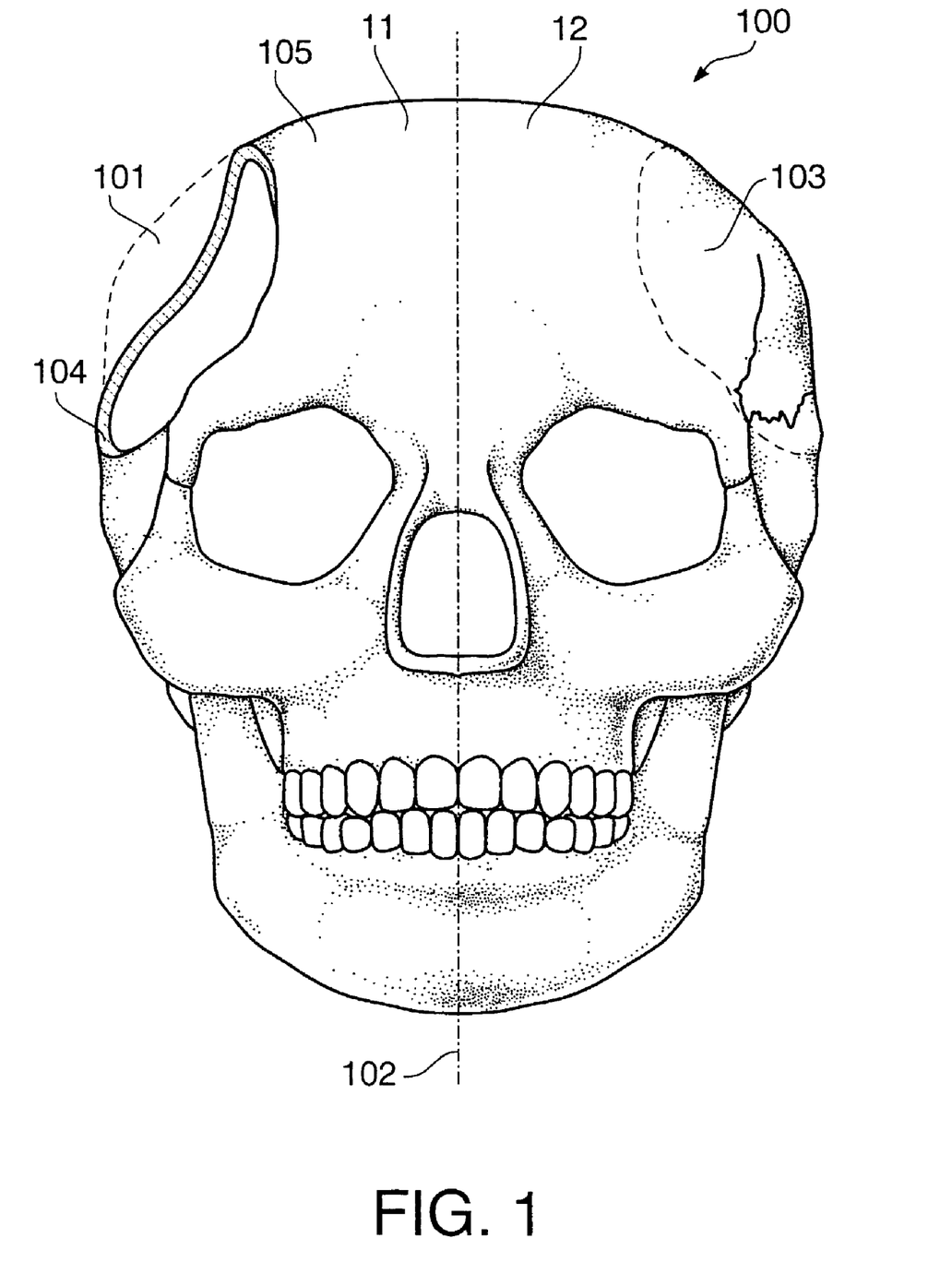
FIG. 1 shows an image of bones of skull generated in accordance with three-dimensional data, which is generated based on a plurality of pieces of tomography data.
Figure 2:
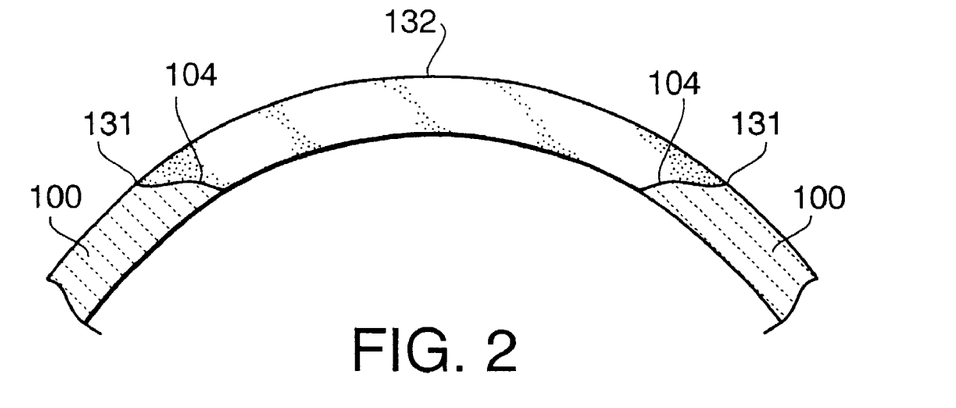
FIG. 2 shows a cross-sectional view of an outer surface of a missing portion which should exist at the deficient portion overlaid with the deficient portion of the body of bone.
Figure 3:
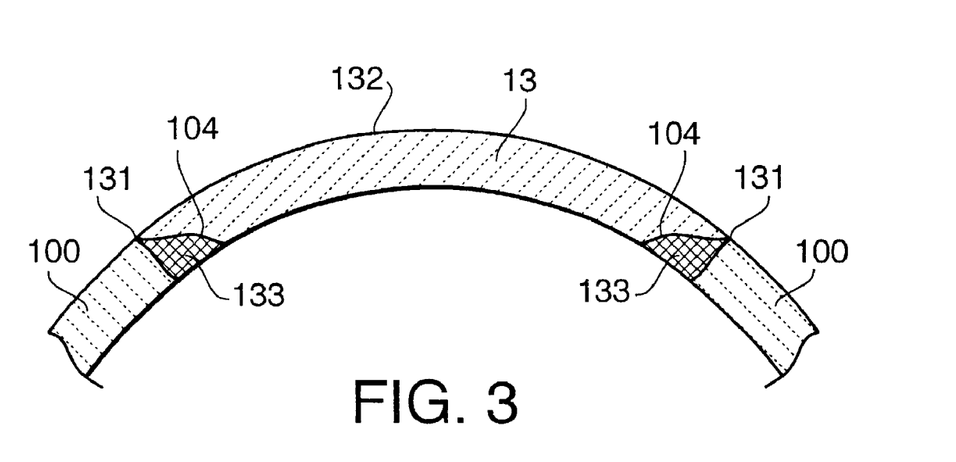
FIG. 3 shows a cross-sectional view of the missing portion having a predetermined thickness overlaid with the deficient portion of the body of bone.
Figure 4:
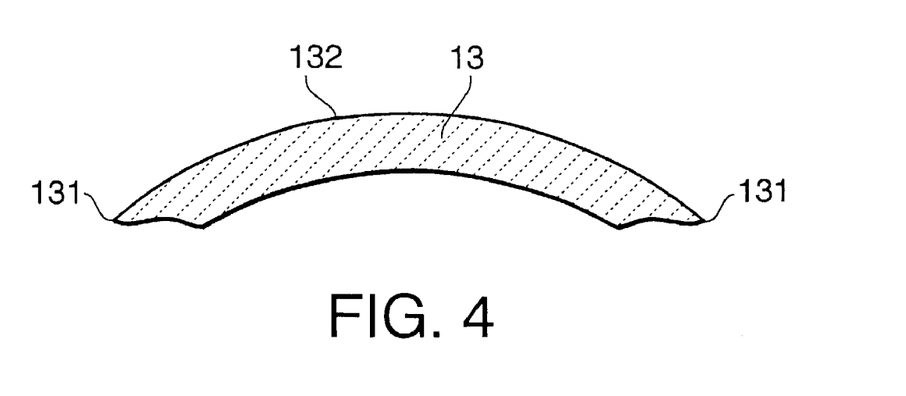
FIG. 4 is a cross-sectional view of the missing portion represented by missing portion data, which is processed such that it matches the bone cutting surface of the body of bone along the thickness direction thereof.

FIG. 1 shows an image of body of bone (i.e., skull) generated in accordance with three-dimensional data, which is generated based on a plurality of pieces of tomography data. FIG. 2 is a drawing showing a condition where outer surface shape data of a bone that should exist at a bone deficient portion is overlapped with the bone deficient portion, FIG. 3 is a drawing showing a condition where bone deficient portion data with a predetermined thickness is overlapped with the bone deficient portion, and FIG. 4 is a drawing showing bone deficient portion data that has been processed so as to match with the bone cutting surface throughout the entirety in the direction of thickness of the bone. In FIG. 2 through FIG. 4, the upper side shows the outer surface side of the bone three-dimensional data, and the lower side shows the inner surface side of the bone three-dimensional data.

According to one aspect of embodiment, a missing portion corresponding to the deficient portion of the body of bone is estimated using a symmetric property of the body of bone. It should be noted that the body of bone for which an implant is formed may be any type of body of bone if it is substantially symmetrical with respect to a certain plane.

According to another aspect, the missing portion is formed so as to fit onto a bone cutting surface of the deficient portion. For this purpose, the body of bone for which an implant is formed may be any type of body of bone.

Examples of such a body of bone include the skull, cheekbone and jaw bone. In the description below, the skull bones used as the body of bone, is substantially symmetrical with respect to a certain plane, having a deficient portion.

Data of Three-Dimensional Structure

Firstly, data 100 (hereinafter referred to as three-dimensional data 100) representing a three-dimensional structure of the bone having the deficient portion as shown in FIG. 1 is prepared. The three-dimensional data 100 is prepared based on a plurality of pieces of tomographic data corresponding to a plurality of slices, respectively. As tomographic data, for example, a CT film and CT data (data outputted from a CT device) can be used.

By organizing the plurality of pieces of tomographic data so as to represent stacked slices of the body of bone, the three-dimensional data 100 can be obtained.

A slicing interval of the tomographic data (distance between adjacent pieces of tomographic data) is not limited to a particular value, however, it is preferably 0.1 mm through 5 mm, and more preferably 0.3 mm through 3 mm.

If the slicing interval is less than the lower limit, depending on the size of the implant, the required number of pieces of tomographic data becomes excessively large. In such a case, the time required for preparing the three-dimensional data 100 is extended, and the accuracy of the three-dimensional data 100 substantially levels off. Accordingly, it may become difficult to further improve the dimensional accuracy of the implant.

If the slicing interval exceeds the upper limit, the accuracy of the three-dimensional data 100 may become insufficient.

It is preferable that the three-dimensional data 100 is obtained by layering a plurality of pieces of tomographic data and further smoothing the surface. Thereby, reproducibility of the implant is well improved.

Estimate of Shape of Missing Portion

Based on the three-dimensional data 100 thus obtained, the shape of the bone that should exist at the bone deficient portion 101 is estimated, and the shape of the missing portion is obtained as three-dimensional data (hereinafter referred to as deficient portion data 13).

Estimate of Outer Surface of Missing Portion

The deficient portion data 13 can be obtained by the following method.

To obtain the deficient portion data 13, first, based on the three-dimensional data 100 that has been obtained as mentioned above, outline data 131 representative of the outer surface of a body of bone that should exist at the deficient portion 101 (i.e., the missing portion) is obtained.

As the outline data 131, outline data representing the outer surface side of a bone cutting surface 104 represented by the three-dimensional data 100 can be used as it is. However, if the three-dimensional data 100 represents a bone substantially symmetrical with respect to a certain plane, it is preferable that the outline data is obtained by the following method.

First, the body of bone represented by the three-dimensional data 100 is divided at a plane 102 of substantial symmetry. The plane 102 is a plane perpendicular to a plane of FIG. 1. With respect to the plane 102, the body of bone is divided into a half section 11 which has the bone deficient portion 101 and a half section 12 which does not have the bone deficient portion 101 are supposed.

Next, at least a part of the outer surface shape data of the half section 12 is inverted, with respect to the symmetry plane 102, to the half section 11 side. It should be noted that the outer surface shape data of the half section 12 to be inverted is only required to include the shape data of a portion 103, which is symmetrical to the bone deficient portion 101 (or, the missing portion) with respect to the symmetry plane 102.

When the outer surface shape data of the half section 12 is inverted, a portion which overlaps the inverted shape is a part of the non-deficient portion 105. Therefore, in the outer surface shape data representing the inverted half section 12, only a portion that does not overlap the outer surface shape of the half section 11 is extracted, whereby the outer surface shape (outer surface shape data 132) of the implant to be applied to the bone deficient portion 101 can be determined (see FIG. 2). The outline 132 of the outer surface shape data thus obtained represents the outline 131 which is required to be determined.

By determining the outline 131 as described above, even if, for example, the shape of the outline at the outer surface side of the bone cutting surface 104 is not clear, sufficiently accurate outline data 131 can be obtained.

Further, if such a method is used, as described above, shape data (outer surface shape data 132) of the entire outer surface of the missing portion that is a bone that is to exist at the bone deficient portion 101 is obtained along with the outline 131. Since the outer surface shape 132 is obtained as described above, even a complicated shape including minute unevenness the bone originally has, can be estimated. As a result, the implant to be designed becomes excellent particularly in shape suitability to the bone.

In the abovementioned method, since the outer surface shape of the missing bone that should exist at the bone deficient portion 101 is estimated using shape data of a part of the bone (shape data representing the outer surface shape of the deficiency symmetrical portion 103), shape suitability to the bone becomes excellent even when the implant to be designed is comparatively large.

Data representing the outer surface shape 132 thus estimated is preferably at the same surface position as that of the outer surface of the body of bone represented by the three-dimensional data 100. Thereby, the finally obtained implant becomes excellent particularly in shape suitability to the bone.

In the method described above, the outline data 131 and the outer surface shape data 132 are obtained simultaneously. However, these pieces of data may be separately obtained. For example, the outer surface shape data 132 is determined after the outline data 131 is obtained.

Estimate of the Thickness of Implant

Using the outer surface shape data 132 estimated as described above, the shape of the implant having a predetermined thickness is estimated, and the bone deficient portion data 13 is obtained. Normally, the thickness of the implant is estimated based on the thickness of the non-deficient portion 105.

Generally, the side surface of the obtained bone missing portion data 13 (surface that should come into contact with the bone cutting surface 104) is substantially flat and smooth without unevenness along the direction of thickness.

It should be noted that the missing portion data 13 may be any type as long as the data is three-dimensional data which is a group of points, lines, plane data or the like.

Estimate of Shape of Contact Surface

Generally, the bone cutting surface of a body of bone having a bone deficient portion is minutely uneven, and does not have a fixed shape along the direction of thickness thereof. Typically, the area of the bone deficient portion tends to be larger at the outer surface side thereof, and smaller at the inner surface side. It is because, when an implant is to be put at the deficient part, in order to prevent the implant from sinking inward, the body of bone is cut such that the outer area is greater and the inner area is smaller.

Therefore, when the missing portion data 13 obtained as described above is overlapped with the bone deficient portion 101 of the three-dimensional data 100, a part of the missing portion data 13 overlaps the non-deficient portion 105 of the three-dimensional data 100. The overlapped portion defines an overlapping portion 133 (a roughly triangular section shown by the lattice pattern). If this overlapping portion 133 is remained, the designed implant does not match the bone cutting surface when applied to the body of bone having the bone deficient portion.

Therefore, according to the embodiment, the missing portion data 13 is corrected so as to fit the shape of the bone cutting surface 104 so that the missing portion data 13 does not overlap the three-dimensional data 100. With this correction, it is ensured that the finally obtained implant fits the bone cutting surface of the body of bone.

Such correction is carried out by eliminating the data corresponding to the overlapping portion 133 from the missing portion data 13. That is, part of the missing portion data 13 at portions where the missing portion data 13 and non-deficient portion 105 overlap each other when the outer surface shape data 132 matches the outline of the outer surface side of the bone cutting surface 104 is eliminated (see FIG. 4).

As a result, an implant that is formed based on the missing portion data 13 thus corrected well corresponds to the shape of the bone cutting surface of the body of bone, and the implant becomes excellent in stability when it is applied to the bone.

Furthermore, according to the embodiment, an implant is designed so as to match the shape of the bone cutting surface of the body of bone, and therefore, trimming that has been conventionally applied to an implant during an operation can be omitted or simplified. As a result, it becomes possible to shorten the operation time, and also to reduce the burden on a patient.

The missing portion data 13 obtained as described above can be used as implant shape data as it is. Optionally, the data may be further corrected as necessary. A correction to be applied to the missing portion data 13 may include a change of the curvature, thickness and the like of at least a part of the implant. With such a correction, a finally obtained implant becomes excellent in shape suitability to the bone, and the stability of the finally obtained implant is further improved.

Implant Forming Method

Next, an implant forming method will be described. An implant is formed based on the above-described design data. It should be noted that, when an implant is formed, shape data obtained by the above-described designing method may be subjected to various processing such as rotation processing.

Hereinafter, the implant forming method will be described in detail.

FIGS. 5 through 9 show cross-sectional views of an implant forming apparatus 1 at various stages of an implant forming method in accordance with an embodiment of the invention. FIG. 10 shows an example of an implant formed in accordance with the method.

Figure 5:
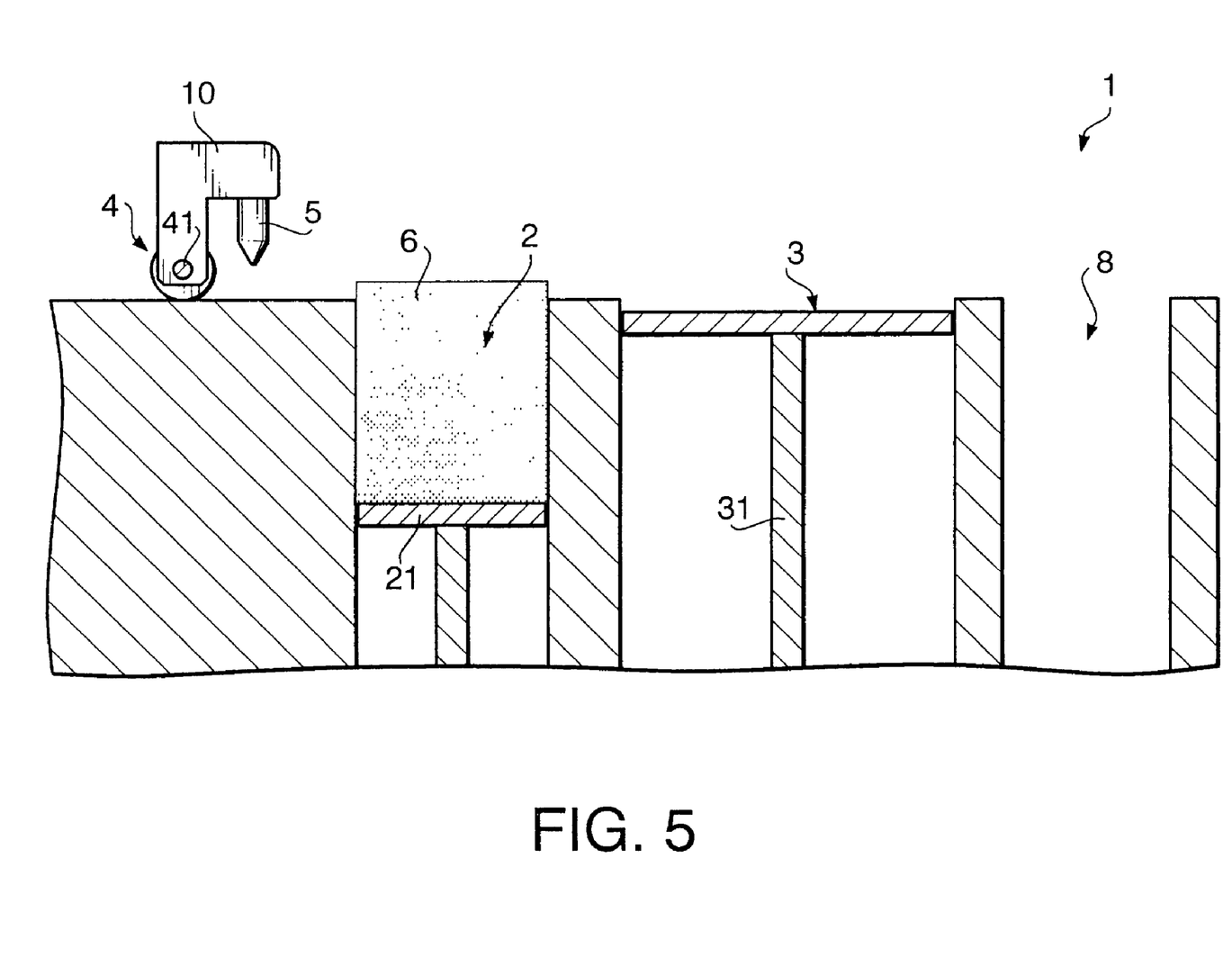
FIG. 5 shows an implant manufacturing apparatus for manufacturing an implant in accordance with a method according to an embodiment of the invention.

As shown in FIG. 5, the implant forming apparatus 1 has an ingredient supplying tank 2, an implant forming stage 3, a roller 4 and a supplying head 5. It should be noted that the implant forming apparatus 1 has a certain width in a direction perpendicular to a surface of the drawing.

In the ingredient tank 2, powdered ingredient 6 used for forming an implant 9 is stored. A bottom 21 of the ingredient material tank 2 has a piston structure 31, which is movable in a vertical direction (i.e., in an up-down direction in FIG. 5). Since various mechanisms have been conventionally known, and any of such mechanisms can apply to the implant forming apparatus 1, the piston mechanism will not be described in detail.

Figure 7:
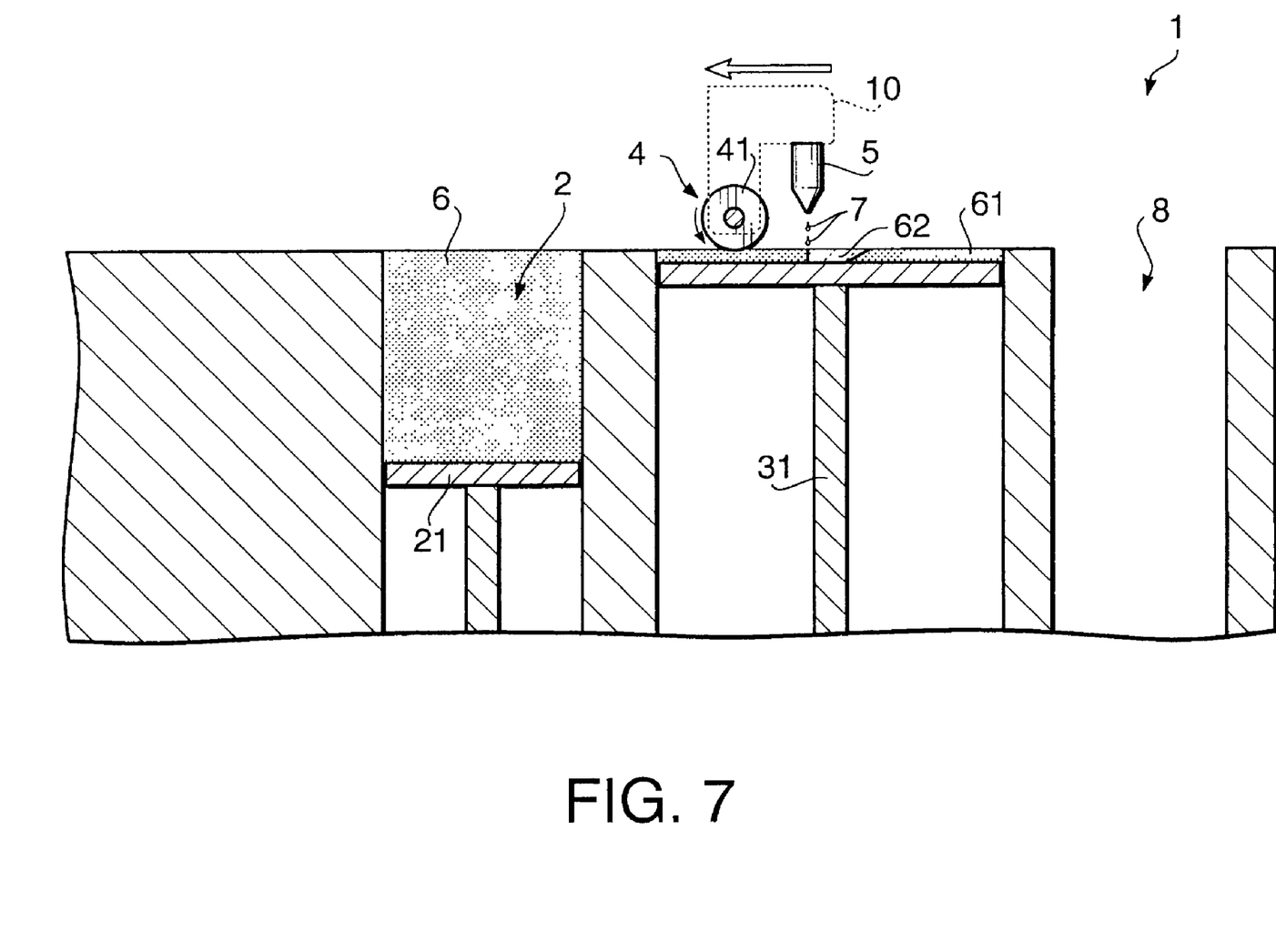
FIG. 7 shows the implant manufacturing apparatus when a second step of the manufacturing method is performed.

The ingredient material is carried from the ingredient material tank 8 to the implant forming stage 3, on which the ingredient material 6 is reacted with reactant liquid 7 to form the implant (see FIG. 7). The implant forming stage 3 is also provided with a piston mechanism 31, and movable in the vertical direction (i.e., in the up-down direction in FIG. 5).

The roller 4 is supported by a supporting device 10 so as to rotatable about a shaft 41 that is held in the supporting device 10. The supporting device 10 is movable in a horizontal direction (i.e., in right- and left-hand direction in FIG. 5). As the supporting device 10 moves in the horizontal direction, the roller rotates and moves on the ingredient material supplying tank 2 and the implant forming stage 3. As will be described in detail below, as the roller moves, some of the powered ingredient 6 is carried onto the implant forming stage 3 to form a layer 61 of the ingredient on the implant forming stage 3.

The liquid supplying head 5 is held by the supporting device 10, and is configured to blow out the reactant liquid 7 toward at least a part of the ingredient layer 61 on the implant forming stage 3.

Figure 6:
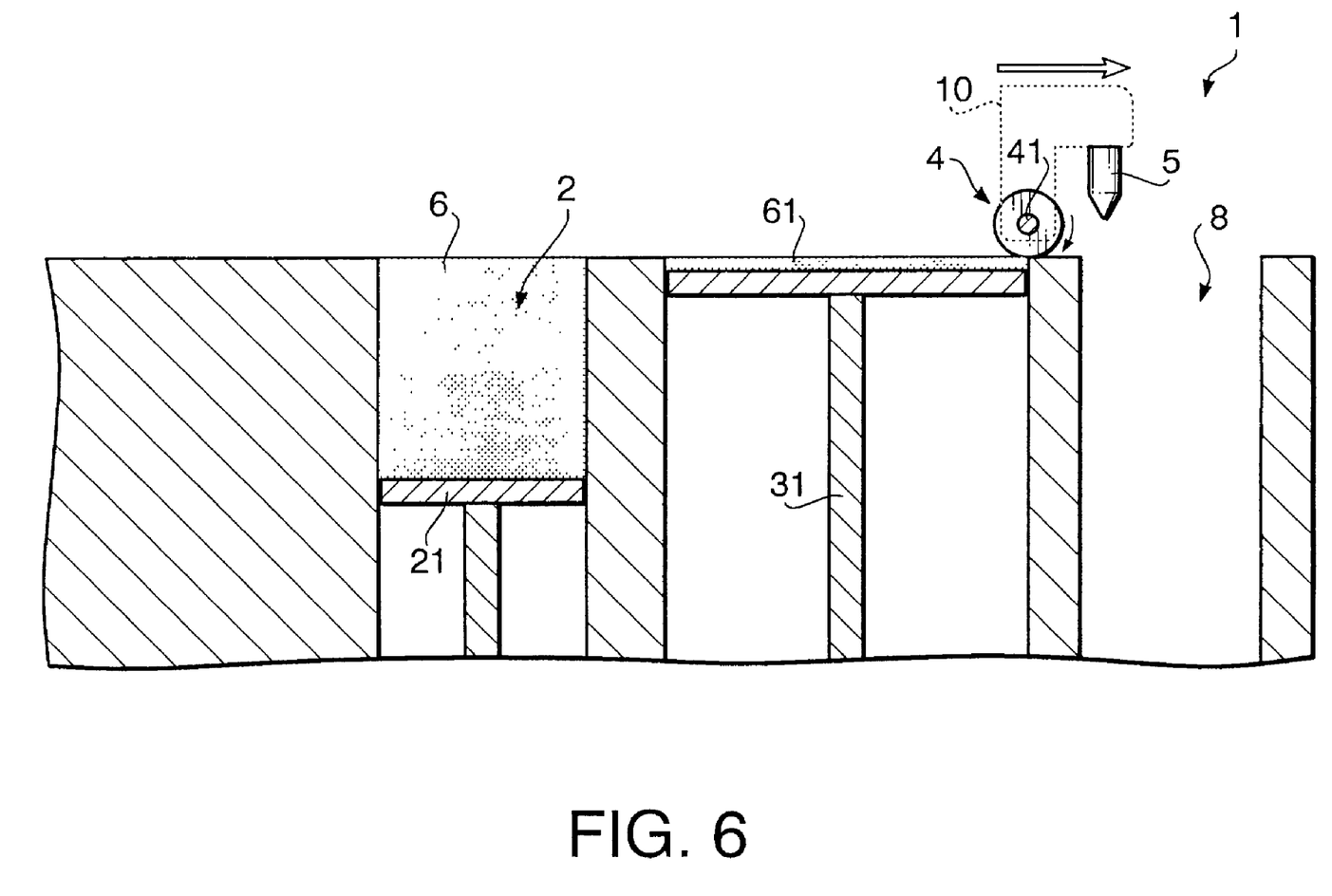
FIG. 6 shows the implant manufacturing apparatus when a first step of the manufacturing method is performed.
Figure 8:
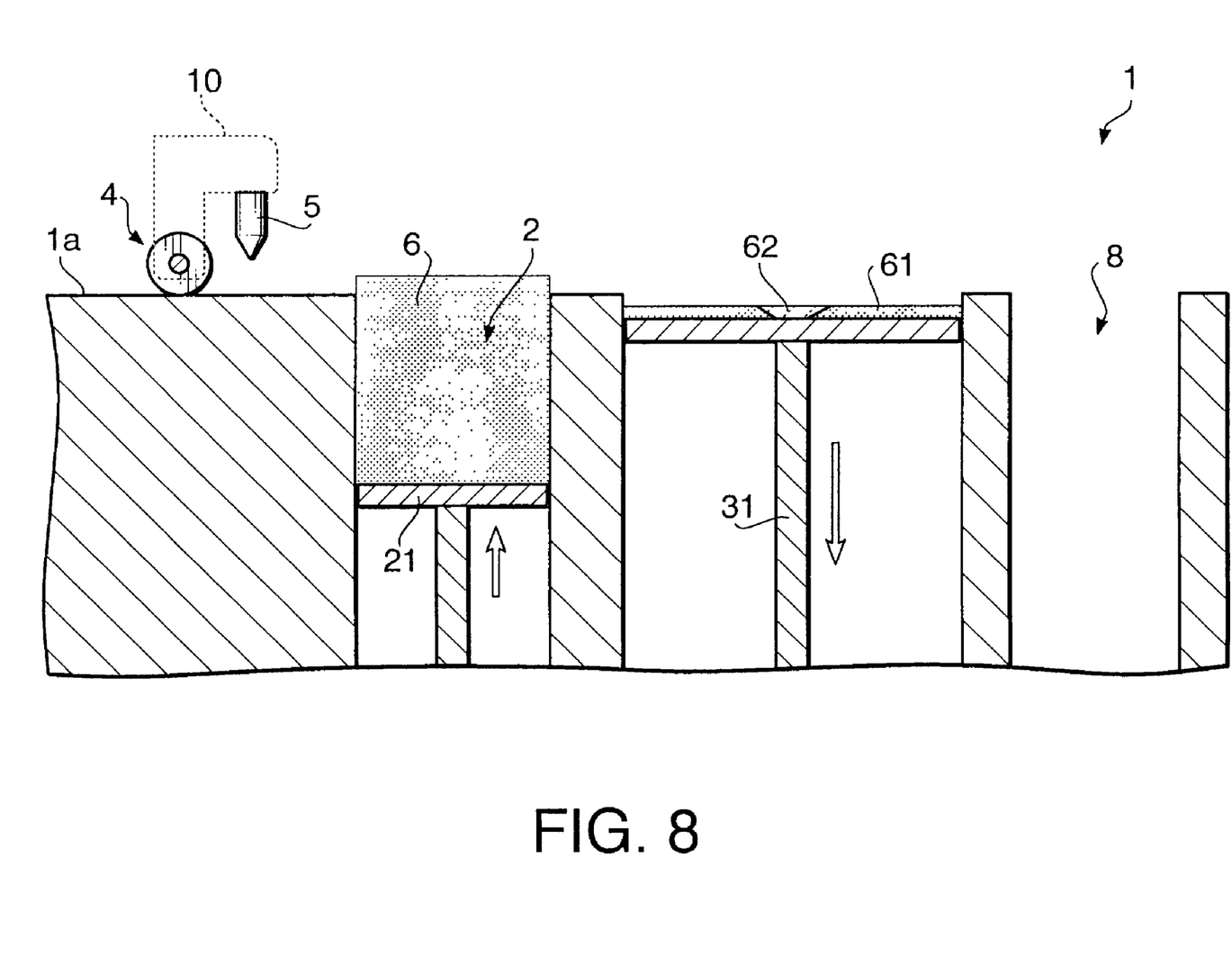
FIG. 8 shows the implant manufacturing apparatus when a third step of the manufacturing method is performed.

A method for forming the implant using the above-described implant forming apparatus 1 will be described in detail with reference to FIGS. 6 through 8.

The method includes the steps of:
(a) forming a layer of powdered ingredient on the implant forming stage;
(b) blowing out the reactant liquid to at least a part of the layer of the powered ingredient; and
(c) moving the implant forming stage downward, and repeating (a) and (b).

Each step will be described in detail hereinafter.

When the powdered ingredient is slightly protruded with respect to a plane of a top surface of the apparatus 1, on which the roller 4 contacts, as shown in FIG. 5, the supporting device 10 is moved to pass over the ingredient material tank 2 and the implant forming stage 3 (i.e., the supporting device 10 moves from the left-hand side of the ingredient material tank 2 to the right-hand side end of the implant forming stage 3. FIG. 6 shows a status when the above movement is finished.

With this movement, the roller 4 moves, with rotating about the shaft 41, carries the protruded portion of the powdered ingredient in the ingredient material tank 2 onto the implant forming stage 3 to form the layer 61.

The mean thickness of the layer 61 is not limited to a specific value, and is determined based on characteristics of the powdered ingredient and the reactant liquid. Generally, the mean thickness may be in a range of 0.1 mm through 0.5 mm. Preferably, the mean thickness is in a range of 0.1 mm through 0.3 mm.

If the mean thickness is too small, a dispersion of the thickness of the layer 61 tends to increase. Further, if the implant 9 to be formed is relatively large in size, a time period for forming the entire implant may become long, which lowers a productivity of the implant.

If the mean thickness is too large, the reactant liquid 7 may not cause sufficient reaction, and a mechanical strength of the resultant implant may not be sufficient. Further, the accuracy in size tends to be lowered.

It should be noted that residual powdered ingredient, which is carried from the ingredient material tank 2 and does not contribute to form the layer 61 is collected by an ingredient collection tank 8.

Next, the reactant liquid 7 is applied to a part of the layer 61 formed on the implant forming stage 3. Then, between the powdered ingredient layer 61 and the reactant liquid 7, chemical reaction is induced, thereby the powdered ingredient 6 is hardened to form hardened section 62.

It should be noted that, according to the embodiment, the ingredient 6 is hardened by the chemical reaction between the ingredient 6 and the reactant liquid 7. That is, the powdered ingredient 6 can be hardened without adjunction of binding agent. Therefore, it is possible to form an implant including less impurities. Such an implant is expected to have an excellent biocompatibility to living body.

According to the embodiment, the reactant liquid 7 is supplied from the supplying head 5 as drops of the liquid. Since the reactant liquid 7 is supplied as described above, the reactant liquid 7 can be supplied with a high accuracy and efficiently to designated portion of the powdered ingredient 6. As a result, the accuracy of the implant in size can be improved, and the productivity is also improved.

As shown in FIG. 7, in the step of supplying the reactant liquid 7, the supplying head 5 moves across above the ingredient material tank 2 and the implant forming stage 3 in the substantially horizontal direction, and supplies the drop of reactant liquid 7 so that portions corresponding to a desired pattern are formed to be the hardened section 62. The desired pattern is generally determined based on the data extracted from the CT film and the like. If it is known that the hardened section 62 shrinks during following process, the pattern is determined taking the shrinking effect into account.

Next, by moving the bottom plate 21 of the ingredient material supplying tank 2 upward to adjust a position of the upper surface of the powdered ingredient (i.e., the protruded amount thereof). At the same time, the implant forming stage 3 is lowered to adjust a position of the upper surface of the layer 61 (i.e., the height of a layer 61 formed by the successively supplied ingredient). The moving amount of the bottom plate 21 preferably corresponds to an amount of the ingredient supplied from the ingredient material supplying tank 2 to the implant forming stage 3 at the first step.

Further, the moving amount of the implant forming stage 3 is preferably the same as the average thickness of the layer 61 formed in the first step. With the above configuration, the thickness of each of the layers 61 is maintained substantially constant.

Figure 9:
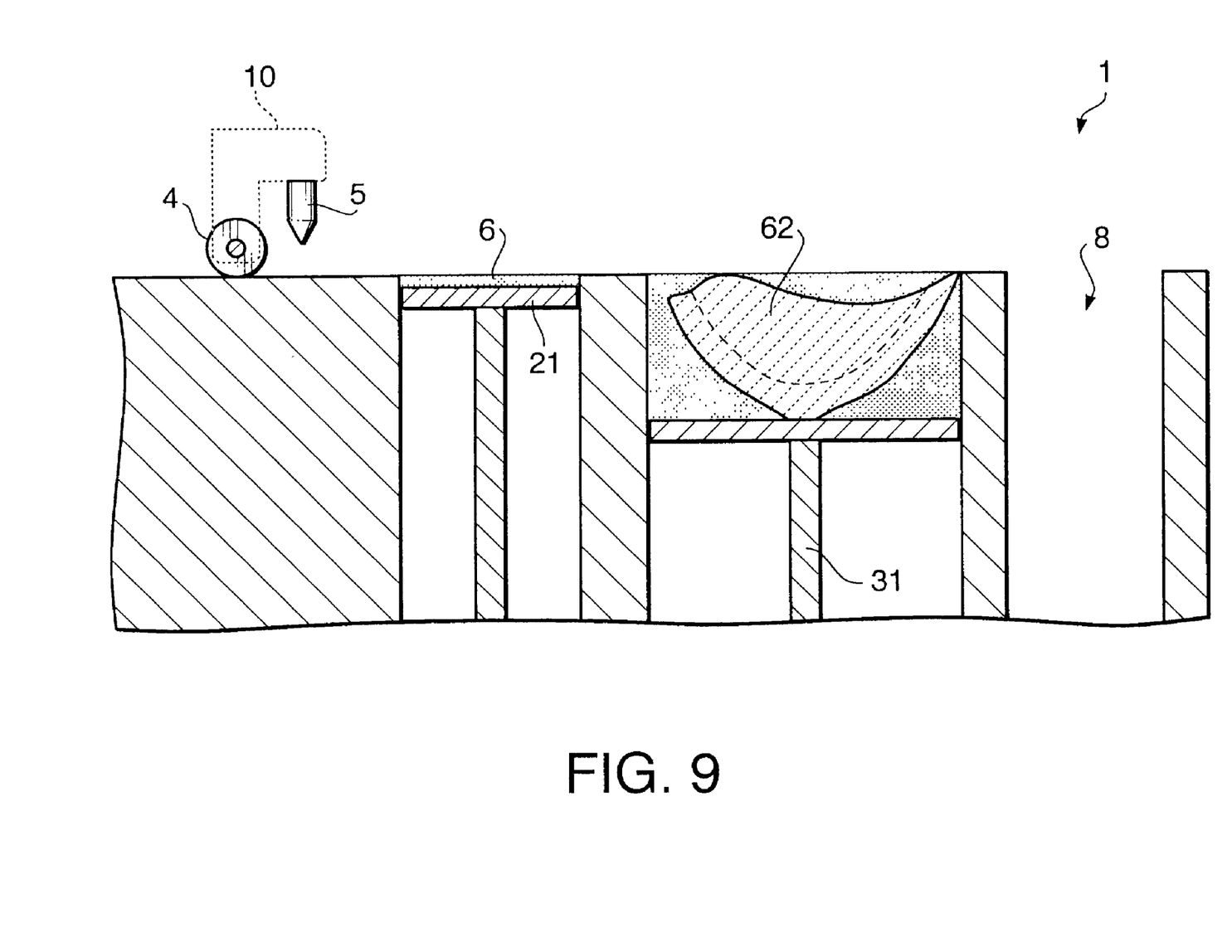
FIG. 9 shows the implant manufacturing apparatus after the first through third steps of the manufacturing method have been performed.
Figure 10:
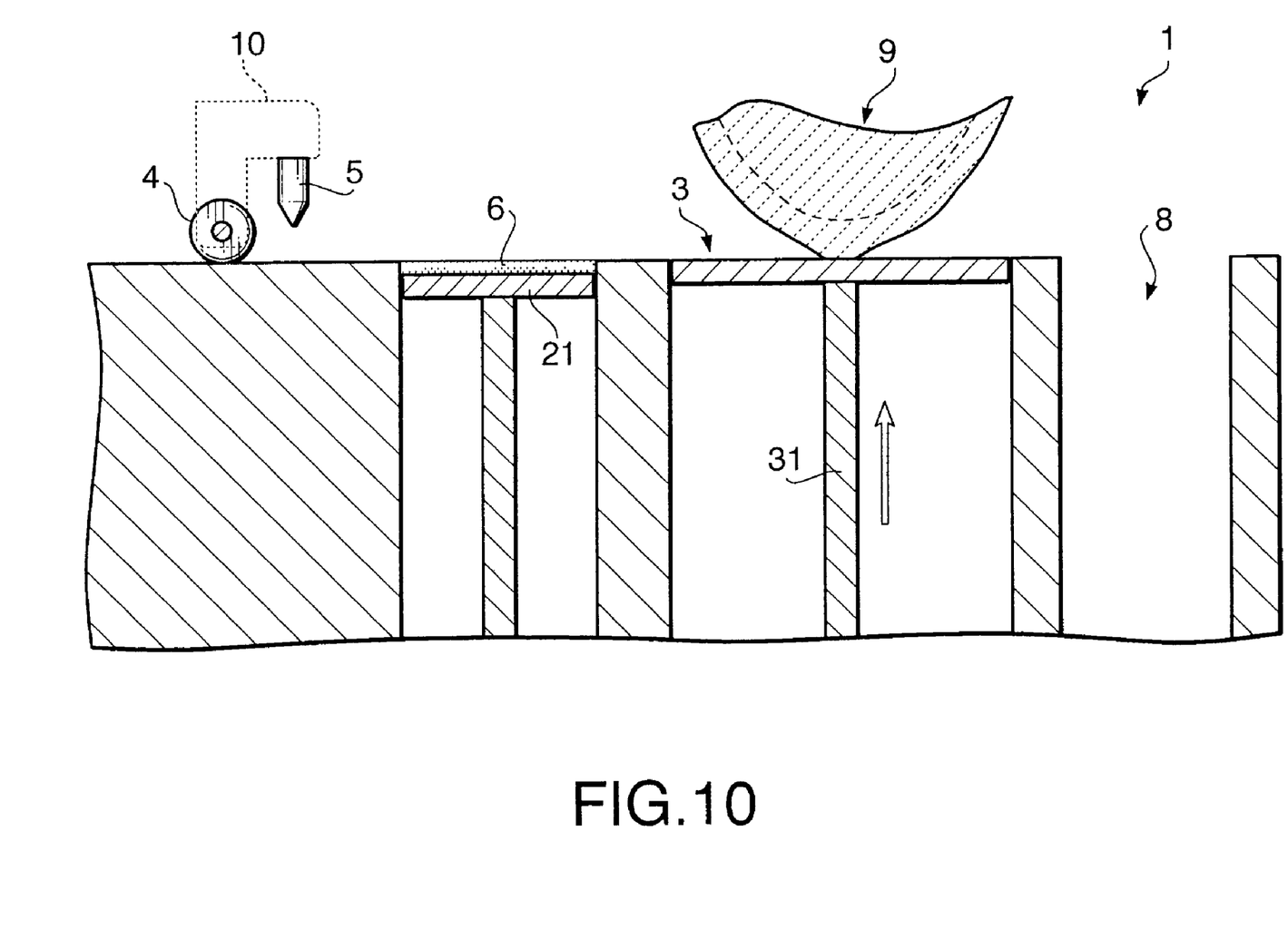
FIG. 10 shows the implant obtained by repeating the first through third steps.

Repeating the first through third steps, a plurality of layers 61 are stacked as shown in FIG. 9, and the hardened portion 62 forms a desired implant shape.

As described above, by stacking the hardened portion 62 of each layer 61, the implant 9 is formed. According to this process, even if the implant 9 has a relatively complicated shape, it can easily be formed. Further, the obtained implant 9 has excellent dimensional accuracy. Furthermore, according to this process, a desired implant 9 can be formed within a relatively short period of time. Therefore, the implant 9 can be formed even when an emergent operation is to be performed.

After the implant forming process is completed, the implant forming stage 3 is lifted and unhardened ingredient powder 6 is removed, thereby the implant 9 having the desired shape is obtained. The unhardened ingredient powder 6 may be removed easily, for example, by blowing air.

The implant 9 thus obtained may be subject to treatment such as sintering or impregnation with a chemical agent (a bone morphogenic agent such as BMP or TGF, or a bone inducer such as PG) as necessary.

It is preferable that the implant 9 thus obtained has an appropriate porosity so that, when the implant 9 is implanted in a living body, osteoblast easily invades in the pores of the implant 9, and bone formation smoothly proceeds. As a result, the period until a stable effect of the implant 9 is obtained can be shortened. The porosity of the implant 9 is, for example, preferably 10 through 90 vol %, and more preferably 30 through 80 vol %.

If the porosity of the implant 9 is too small, the osteoblast may not invade in the pores of the implant 9 sufficiently, and bone formation does not proceed well.

If the porosity of the implant 9 is too large, a sufficient mechanical strength of the implant 9 may not be obtained.

The pores formed in the implant 9 are preferably continuous pores, whose mean diameter is 100 µm or more. If the pore diameter is less than 100 µm, the osteoblast does not invade in the pores of the implant 9 sufficiently, and bone formation may not proceed well. If the pore diameter is too large, however, sufficient mechanical strength of the implant 9 may not be obtained.

As described above, the ingredient material powder 6 is hardened by chemical reaction between the ingredient material powder 6 and the reactant liquid 7. Therefore, the ingredient material powder 6 can be hardened without adding a binder. Accordingly, the implant 9 includes less impurities, and thus, it has excellent biocompatibility.

Further, both the ingredient material powder 6 and reactant liquid 7 may have excellent biocompatibility. In such a case, even when the ingredient material powder 6 and reactant liquid 7 remain unreacted, a harmful influence on the living body can be prevented effectively.

Hereinafter, the ingredient material power 6 and the reactant liquid 7 will be described in detail.

<Ingredient Powder>

As the ingredient powder 6, a powder which contains a-tricalcium phosphate, tetracalcium phosphate, and calcium hydrogenphosphate is used.

The a-tricalcium phosphate and tetracalcium phosphate to be used may be separately produced by well-known methods, or a mixture of a-tricalcium phosphate and tetracalcium phosphate which are obtained by sintering hydroxy apatite.

When the hydroxy apatite is sintered, a sintering condition will be 1150° C. through 1450° C. for about one hour under decompression.

The calcium hydrogen phosphate may also be one manufactured by a well-known method, and either anhydride ($CaHPO_4$) or hydrate (for example, dihydrate ($CaHPO_4.2H_2O$), etc.) may be used.

The ingredient powder 6 may further contain, as appropriate, hydroxy apatite, fluoroapatite, β-tricalcium phosphate, and calcium pyrophosphate in addition to the abovementioned three substances.

The ingredient powder 6 according to the embodiment chemically reacts with the reactant liquid 7 and is hardened.

The Ca/P ratio of the ingredient powder 6 is 1.40 through 1.80, and is preferably 1.40 through 1.67. If the Ca/P ratio is less than 1.40 or exceeds 1.80, the hardening reaction does not proceed at a sufficient reaction rate, and the mechanical strength of an obtained implant 9 may be less than necessary.

In the ingredient powder 6, additives such as an X ray contrast medium, an antibacterial agent, a bone morphogenic factor such as BMP or TGF and a bone inducer such as PG may be contained as necessary. The X ray contrast medium is not especially limited, and various X ray contrast media can be used, for example, one or more kinds among barium sulphate, basic bismuth carbonate, and iodoform can be used. As an antibacterial agent, iodoform and chlorhexidine or the like, can be used.

The mean particle size of the ingredient powder 6 is preferably 10 µm through 100 µm, and more preferably 20 µm through 40 µm.

If the mean particle size of the ingredient powder 6 is less than the lower limit (i.e., 10 µm), it becomes difficult to handle the ingredient powder 6. Also, if the average particle size of the ingredient powder 6 is less than the lower limit, the porosity of the obtained implant 6 becomes too low, and the bone formation may not proceed well.

If the mean particle size of the ingredient powder 6 exceeds the upper limit, depending on the size of the implant 9 to be formed by the abovementioned forming process, sufficient dimensional accuracy may not be achieved.

Reactant Liquid

Any type of reactant liquid 7 can be used if it chemically reacts with the ingredient powder 6 and hardens the same. Preferably, the reactant liquid is water or liquid mainly composed of water.

If such a reactant liquid 7 is used, the hardened portion 62 formed by reaction between the ingredient powder 6 and the reactant liquid 7 has a superior mechanical strength. In particular, if water or a liquid mainly composed of water is used as the reactant liquid 7, apatite (hydroxy apatite or octacalcium phosphate) is produced by reaction with the ingredient powder 6. It is known that the apatite has excellent biocompatibility. Therefore, a high-security implant 9 can be provided.

In the reactant liquid 7, as components other than water, various preparations may be contained, for example, organic acids such as acetic acid, lactic acid, citric acid, malic acid, malonic acid, succinic acid, glutaric acid, tartaric acid, polyacrylic acid, and gluconic acid or the like, inorganic acids such as phosphoric acid, a pH regulator, a thickener, an x ray contrast medium, an antibacterial agent, a bone morphogenic factor such as BMP or TGF, and a bone inducer such as PG may be contained.

The reaction liquid 7 may contain insoluble substances if they have sufficient fluidity.

As in the above, the implant forming method and the implant according to the exemplary embodiment have been described, however, the invention is not limited to the described one.

For example, in the abovementioned embodiment, an implant and an implant designing method which are applied to the cranium have been described, however, the implant can be applied to various bones.

Furthermore, in the embodiment, it has been described that the reaction liquid hardens the ingredient powder by chemically reacting therewith, however, the invention is not limited to such a configuration. Namely, any reactant liquid can be used only if the liquid hardens the ingredient powder. For example, as in the case where a liquid containing methyl cellulose and polyvinyl alcohol, any liquid (binder) which hardens the ingredient powder without a chemical reaction can be used.

As mentioned above, according to the invention, an implant which is excellent in reproducibility and/or shape suitability of a bone deficient portion can be provided.

In addition, even when an implant to be formed is relatively large, an implant with excellent reproducibility and/or shape suitability can be provided.

Conventionally, it has been extremely difficult to estimate if the body of bone is a cheekbone or jawbone. According to the above-described embodiment, even in such a case, where the shape of a bone that should exist at a bone deficient portion, an implant with excellent reproducibility can be provided.

The present disclosure relates to the subject matters contained in Japanese Patent Applications No. 2001-262196, filed on Aug. 30, 2001, and No. 2001-357535, filed on Nov. 22, which are expressly incorporated herein by reference in their entireties.

What is claimed is:

1. An implant designing method to be applied to a bone body which has a bone deficient portion, the bone being in substantial symmetry with respect to a plane of symmetry, comprising:
    generating three-dimensional data of the bone based on a plurality of pieces of tomographic data of the bone; and
    estimating a shape of a bone, which is to exist at the bone deficient portion, based directly on part of the three-dimensional data corresponding to a symmetrical part of the bone deficient portion,
    wherein a slicing interval of the tomographic data used for generating the three-dimensional data is within a range of 0.1 mm through 5 mm.

2. The implant designing method according to claim 1, wherein the bone body is a skull.

3. An implant that is formed based on a designing method, which is applied to a bone body which has a bone deficient portion, the bone being in substantial symmetry with respect to a plane of symmetry, the method comprising:
    generating three-dimensional data of the bone based on a plurality of pieces of tomographic data of the bone; and
    estimating a shape of a bone, which is to exist at the bone deficient portion, based directly on part of the three-dimensional data corresponding to a symmetrical part of the bone deficient portion,
    wherein a slicing interval of the tomographic data used for generating the three-dimensional data is within a range of 0.1 mm through 5 mm.

4. An implant forming method for forming an implant to be applied to a bone body which has a bone deficient portion, the bone being in substantial symmetry with respect to a plane of symmetry, the method including:

(a) generating three-dimensional data of the bone based on a plurality of pieces of tomographic data of the bone;

(b) estimating a shape of a bone, which is to exist at the bone deficient portion, based directly on part of the three-dimensional data corresponding to a symmetrical part of the bone deficient portion;

(c) forming a layer composed of an ingredient powder; and (d) hardening a reactant liquid by chemically reacting the ingredient powder with a reactant liquid in accordance with the shape of the implant in accordance with the design, wherein the forming and hardening are repeated to stack a plurality of the layers to form an implant formed of the hardened portion of the layers of the ingredient powder, and wherein a slicing interval of the tomographic data used for generating the three-dimensional data is within a range of 0.1 mm through 5 mm.

5. The implant which is formed in accordance with an implant forming method for forming an implant to be applied to a bone body which has a bone deficient portion, the bone being in substantial symmetry with respect to a plane of symmetry, the method including:

generating three-dimensional data of the bone based on a plurality of pieces of tomographic data of the bone;

estimating a shape of a bone, which is to exist at the bone deficient portion, based directly on part of the three-dimensional data corresponding to a symmetrical part of the bone deficient portion;

forming a layer composed of an ingredient powder; and hardening a reactant liquid by chemically reacting the ingredient powder with a reactant liquid in accordance with the shape of the implant in accordance with the design, wherein the forming and the hardening are repeated to stack a plurality of the layers to form an implant formed of the hardened portion of the layers of the ingredient powder, and wherein the porosity of the implant is within a range of 10 vol % through 90 vol %.

6. An implant designing method to be applied to a bone body which has a bone deficient portion, the bone being in substantial symmetry with respect to a plane of symmetry, comprising:

generating three-dimensional data of the bone body based on a plurality of pieces of tomographic data of the bone; and estimating a shape of the implant to be implanted at the bone deficient portion based directly on the three-dimensional data using a symmetric property of the bone body, wherein a slicing interval of the tomographic data used for generating the three-dimensional data is within a range of 0.1 mm through 5 mm.

7. An implant designing method to be applied to a bone body having a bone deficient portion, comprising:

generating three-dimensional data of the bone body;

estimating the shape of an implant to be implanted to the bone deficient portion based directly on the three-dimensional data; and modifying the three-dimensional data such that at least a part of the implant in a circumferential direction has a shape that fits a corresponding portion of a bone cutting surface of the bone body, wherein a slicing interval of topographic data to be used for generating the three-dimensional data is 0.1 mm through 5 mm.

8. An implant designing method to be applied to a bone body having a bone deficient portion, comprising:

generating three-dimensional data of the bone body;

estimating the shape of an implant to be implanted to the bone deficient portion based directly on the three-dimensional data; and modifying the three-dimensional data such that at least a part of the implant in a circumferential direction has a shape that fits a corresponding portion of a bone cutting surface of the bone body, wherein a slicing interval of topographic data to be used for generating the three-dimensional data is 0.1 mm through 5 mm, wherein the estimating includes designing a shape of the implant that matches the shape of the outline of the bone cutting surface on the outer surface of the bone body, the implant having a substantially fixed shape in a direction of thickness thereof, and wherein the modifying includes overlapping the data representing at least the bone cutting surface of the bone body and the data of the implant, and eliminating data of the implant corresponding to a portion overlapping the bone body.

9. An implant designing method to be applied to a bone body having a bone deficient portion, comprising:

generating three-dimensional data of the bone body;

estimating the shape of an implant to be implanted to the bone deficient portion based directly on the three-dimensional data; and modifying the three-dimensional data such that at least a part of the implant in a circumferential direction has a shape that fits a corresponding portion of a bone cutting surface of the bone body, wherein a slicing interval of topographic data to be used for generating the three-dimensional data is 0.1 mm through 5 mm, and wherein the estimating includes:

generating outline data representing the outer surface of the implant so as to match with the shape of the outline of the bone cutting surface on the outer surface of the bone body;

estimating the shape of the implant that has a predetermined thickness and a substantially fixed shape in the direction of thickness, using the outline data; and eliminating, from the estimated shape data, data representing a portion overlapping the bone body so that the implant fits the shape of the bone cutting surface.

10. An implant designing method to be applied to a bone body having a bone deficient portion, comprising:

generating three-dimensional data of the bone body;

estimating the shape of an implant to be implanted to the bone deficient portion based directly on the three-dimensional data; and modifying the three-dimensional data such that at least a part of the implant in a circumferential direction has a shape that fits a corresponding portion of a bone cutting surface of the bone body, wherein a slicing interval of topographic data to be used for generating the three-dimensional data is 0.1 mm through 5 mm, and wherein the estimating includes:
generating outline data representing the outer surface of the implant so as to match with the shape of the outline of the bone cutting surface on the outer surface of the bone body;
estimating the shape of the implant that has a predetermined thickness and a substantially fixed shape in the direction of thickness, using the outline data;
comparing data representing the shape of the implant which is generated in the estimating with at least part of the three-dimensional data representing the bone cutting surface; and
compensating for the data representing the shape of the implant in accordance with a comparison result of the comparing so that the implant fits the shape of the bone cutting surface.

11. The implant designing method according to claim 7, wherein if the implant is applied to the bone deficient portion, the outer surface of the bone body and the outer surface of the implant come to substantially the same surface position.

12. The implant designing method according to claim 7, wherein the bone body is substantially symmetrical with respect to a predetermined plane, a shape of an implant to be implanted at the bone deficient portion being estimated using shape data representative of a portion symmetrical to the bone deficient portion of the three-dimensional data with respect to a substantial symmetry plane of the three-dimensional data.

13. The implant designing method according to claim 7, wherein the bone is the cranium.

14. An implant forming method to be applied to a bone body having a bone deficient portion, comprising:
generating three-dimensional data of the bone body;
estimating the shape of an implant to be implanted to the bone deficient portion based directly on the three-dimensional data;
modifying the three-dimensional data such that at least a part of the implant in a circumferential direction has a shape that fits a corresponding portion of a bone cutting surface of the bone body;
forming a layer composed of an ingredient powder; and
hardening a reactant liquid by chemically reacting the ingredient powder with a reactant liquid in accordance with the shape of the implant in accordance with the design,
wherein the forming and the hardening are repeated to stack a plurality of the layers to form an implant formed of the hardened portion of the layers of the ingredient powder, and
wherein a slicing interval of tomographic data used for generating the three-dimensional data is within a range of 0.1 mm through 5 mm.

15. The implant which is formed in accordance with an implant forming method to be applied to a bone body having a bone deficient portion,
the forming method comprising:
generating three-dimensional data of the bone body;
estimating the shape of an implant to be implanted to the bone deficient portion based directly on the three-dimensional data;
modifying the three-dimensional data such that at least a part of the implant in a circumferential direction has a shape that fits a corresponding portion of a bone cutting surface of the bone body;
forming a layer composed of an ingredient powder; and
hardening a reactant liquid by chemically reacting the ingredient powder with a reactant liquid in accordance with the shape of the implant in accordance with the design,
wherein the forming and the hardening are repeated to stack a plurality of the layers to form an implant formed of the hardened portion of the layers of the ingredient powder, and
wherein the porosity of the implant is within a range of 10 vol % through 90 vol %.

* * * * *